United States Patent
Heuer

(10) Patent No.: US 10,709,489 B2
(45) Date of Patent: Jul. 14, 2020

(54) EXTENSION DEVICE FOR A BONE SCREW AND SCREWDRIVER INSTRUMENT

(71) Applicant: Silony Medical International AG, Frauenfeld (CH)

(72) Inventor: Frank Heuer, Filderstadt (DE)

(73) Assignee: Silony Medical International AG, Frauenfeld (CH)

( * ) Notice: Subject to any disclaimer, the term of this patent is extended or adjusted under 35 U.S.C. 154(b) by 29 days.

(21) Appl. No.: 16/122,103

(22) Filed: Sep. 5, 2018

(65) Prior Publication Data
US 2019/0083156 A1   Mar. 21, 2019

(30) Foreign Application Priority Data
Sep. 7, 2017   (DE) .......................... 10 2017 120 619

(51) Int. Cl.
*A61B 17/88*   (2006.01)
*A61B 17/70*   (2006.01)
(Continued)

(52) U.S. Cl.
CPC ...... *A61B 17/8875* (2013.01); *A61B 17/7032* (2013.01); *A61B 17/7082* (2013.01);
(Continued)

(58) Field of Classification Search
CPC ............ A61B 17/7032; A61B 17/7076; A61B 17/708; A61B 17/7082; A61B 17/7085;
(Continued)

(56) References Cited

U.S. PATENT DOCUMENTS

| 8,512,344 B2 * | 8/2013 | Hoffman ............ A61B 17/8875 606/86 A |
| 8,764,756 B2 * | 7/2014 | Jones ................. A61B 17/7086 606/86 A |

(Continued)

FOREIGN PATENT DOCUMENTS

WO   2017089141 A1   6/2017

OTHER PUBLICATIONS

German Office Actions dated Jun. 13, 2018.

*Primary Examiner* — Larry E Waggle, Jr.
(74) *Attorney, Agent, or Firm* — Dilworth & Barrese, LLP

(57) ABSTRACT

The invention refers to an extension device (1) for a bone screw (4) and to a screwdriver instrument (2) connectable to the extension device (1); it is proposed that the screwdriver instrument (2) comprises a toggle lever mechanism (62) having a first and a second lever arm (64, 66), which are pivotally connected to each other through a common articulation point (68), that the first lever arm (64) may be removably applied, in the area of its free end (70), at a first pivot bearing point (72) on the extension device (1) and is pivotally mounted and axially supported in the applied state, and that the second lever arm (66) is pivotally mounted and axially supported at a second pivot bearing point (74) on the shank, that the first lever arm (64) is elastically and longitudinally extendable, and that this longitudinal extensibility and a distance between the second pivot bearing point (74) and the common articulation point (68) of the lever arms (64, 66) are adapted to each other in such a way that when manually pivoting the second lever arm (66) in the direction of a parallel alignment with the axial longitudinal direction (16), a dead center is overcome, and the toggle lever mechanism (62) reaches a tilt-stable position (60), in which
(Continued)

Figure 3D:
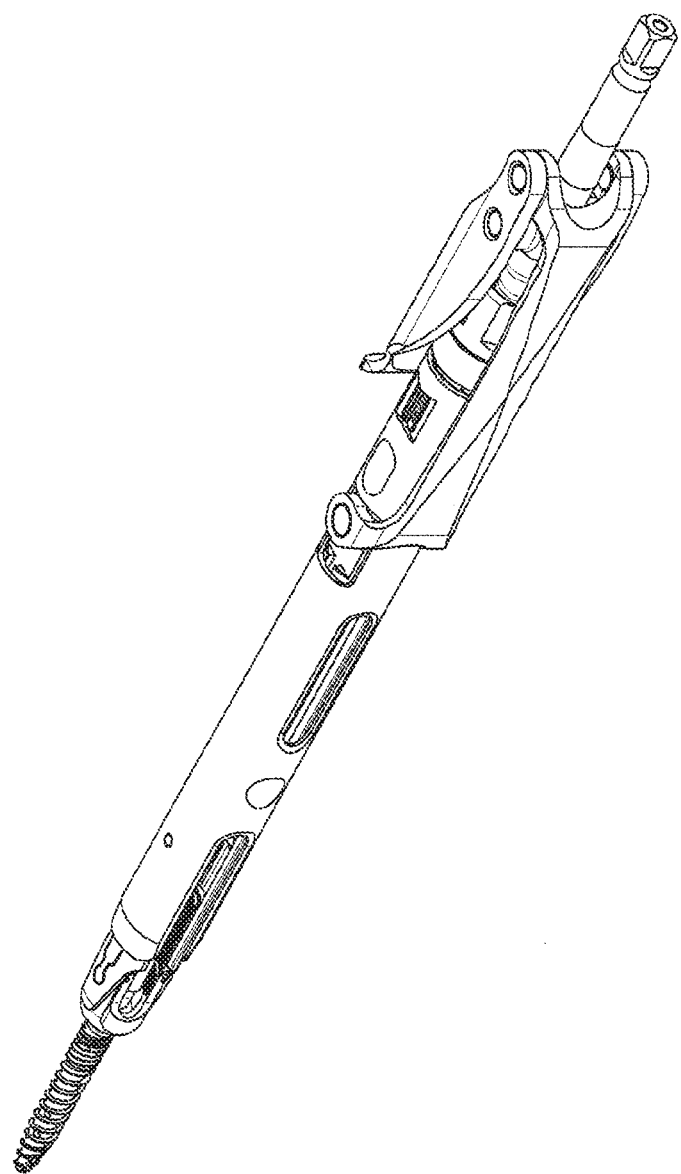

the shank of the screwdriver instrument (2) is forced in the axial direction (16) against the tool application point of the bone screw.

17 Claims, 8 Drawing Sheets

(51) Int. Cl.
*A61B 17/86* (2006.01)
*A61B 90/00* (2016.01)

(52) U.S. Cl.
CPC ...... *A61B 17/8635* (2013.01); *A61B 17/7037* (2013.01); *A61B 17/7085* (2013.01); *A61B 17/8605* (2013.01); *A61B 2090/037* (2016.02)

(58) Field of Classification Search
CPC . A61B 17/88; A61B 17/8872; A61B 17/8875; A61B 17/8861; A61B 17/8891
See application file for complete search history.

(56) References Cited

U.S. PATENT DOCUMENTS

| | | | |
|---|---|---|---|
| 8,845,652 B2* | 9/2014 | Heinz | B25B 23/101 |
| | | | 606/104 |
| 9,084,642 B2* | 7/2015 | Peultier | A61B 17/7083 |
| 9,615,862 B1* | 4/2017 | Doubler | A61B 17/7076 |
| 2005/0214719 A1* | 9/2005 | Hermann | A61C 3/14 |
| | | | 433/215 |
| 2013/0110179 A1 | 5/2013 | Barrus et al. | |

* cited by examiner

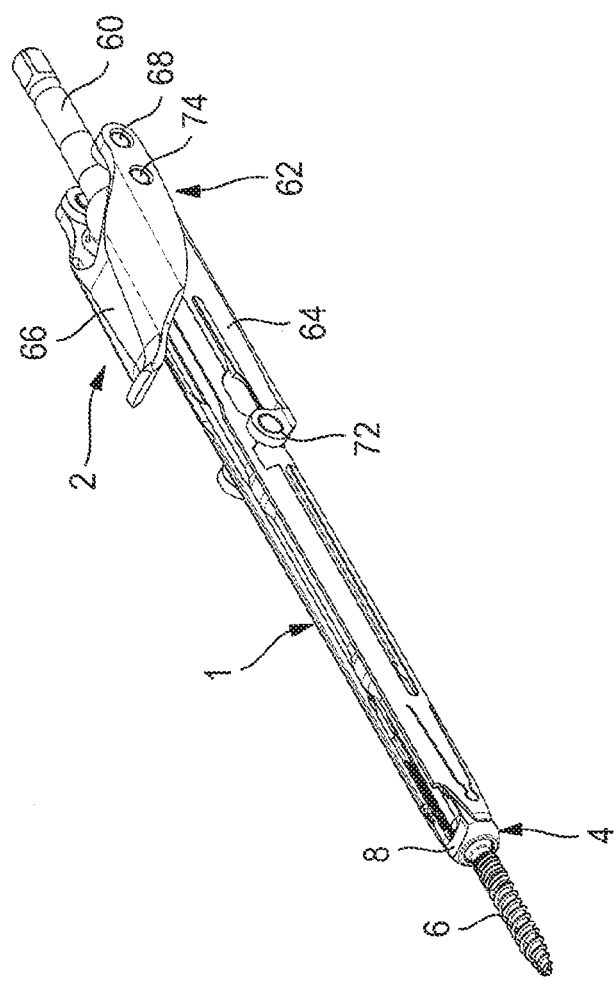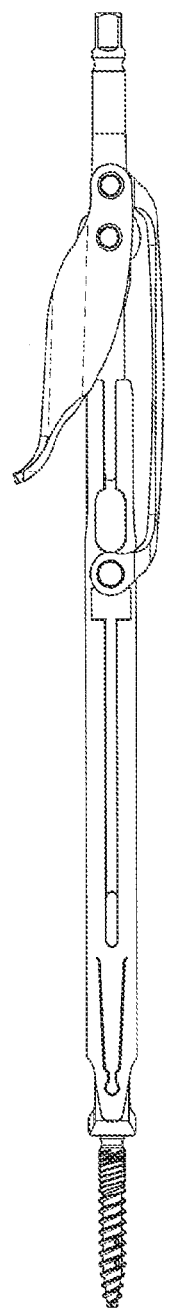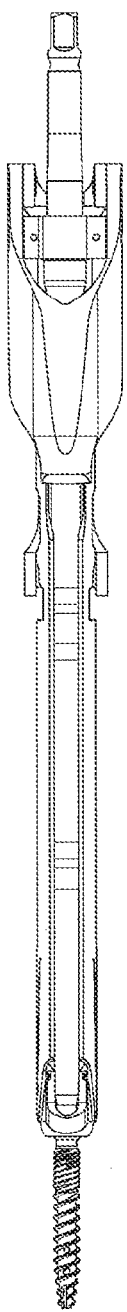

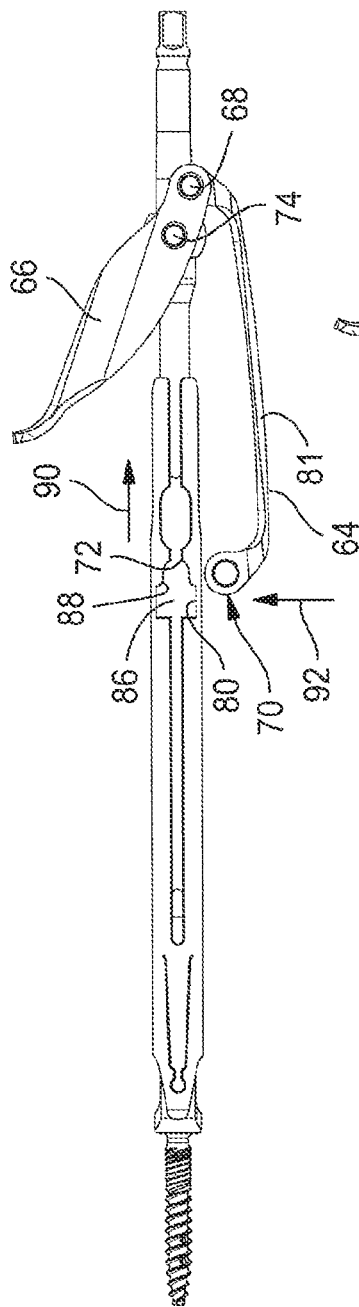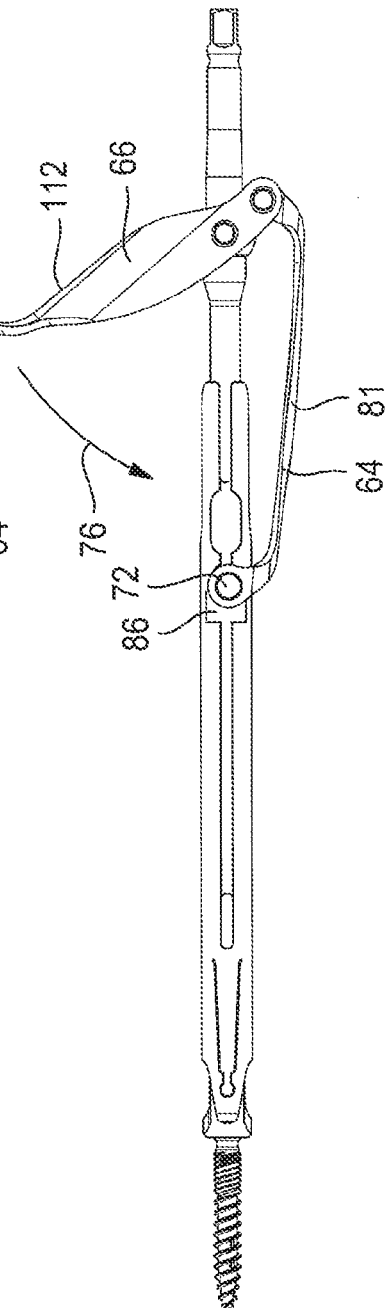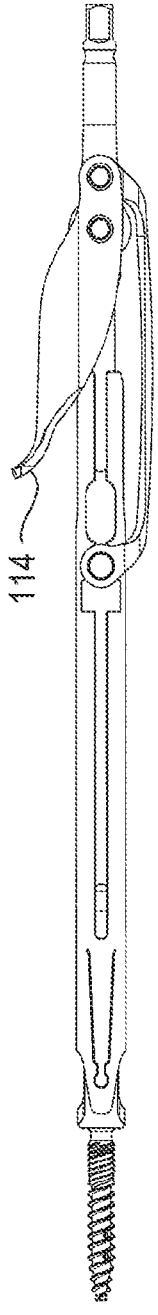

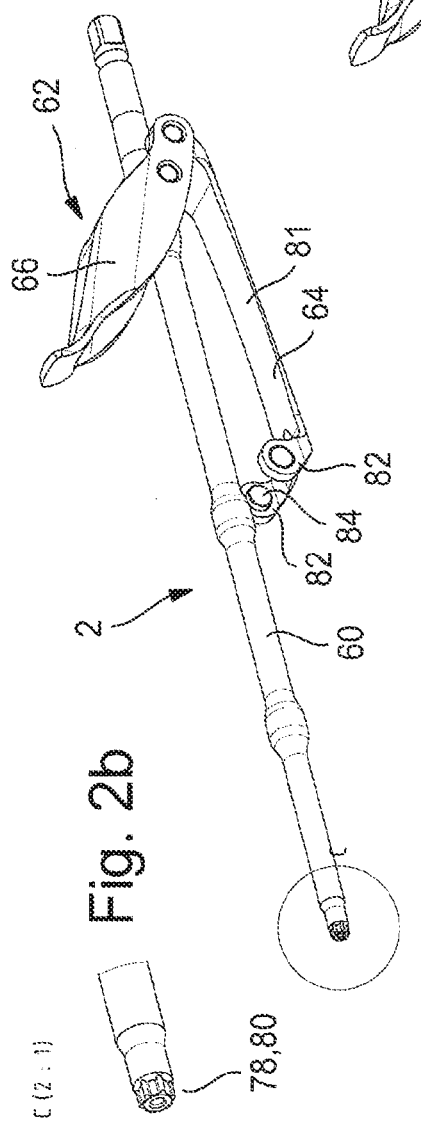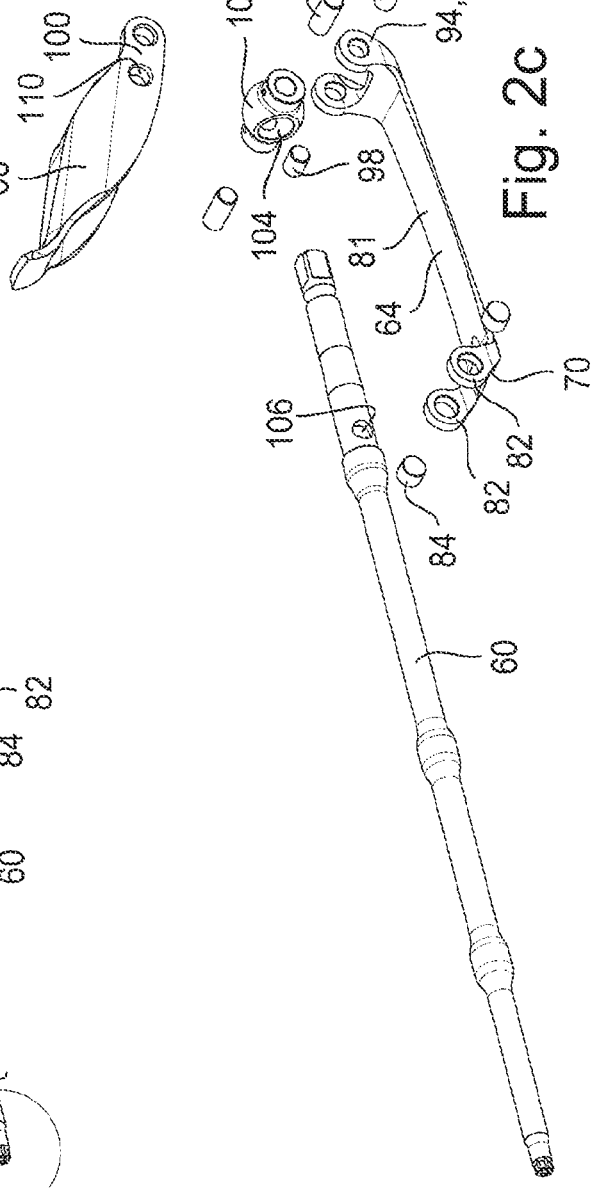

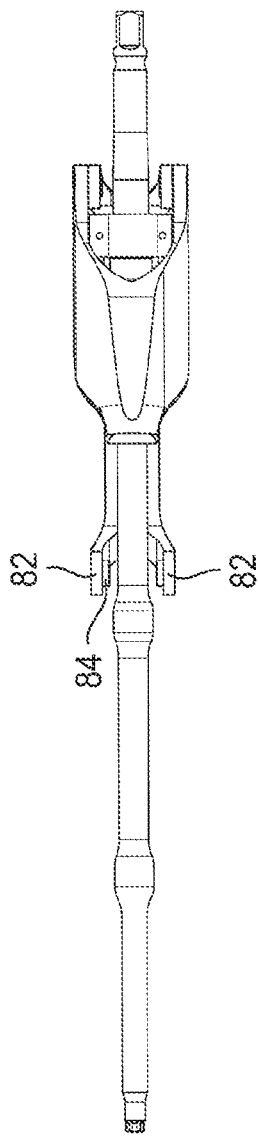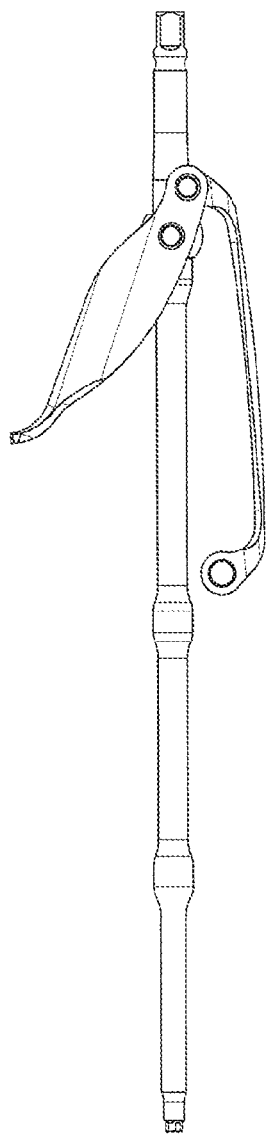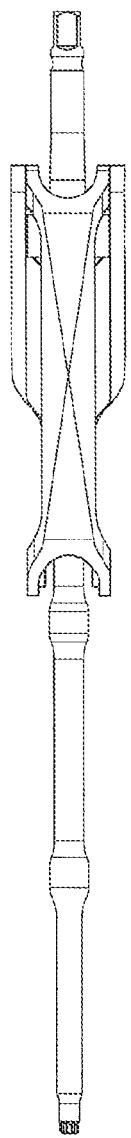

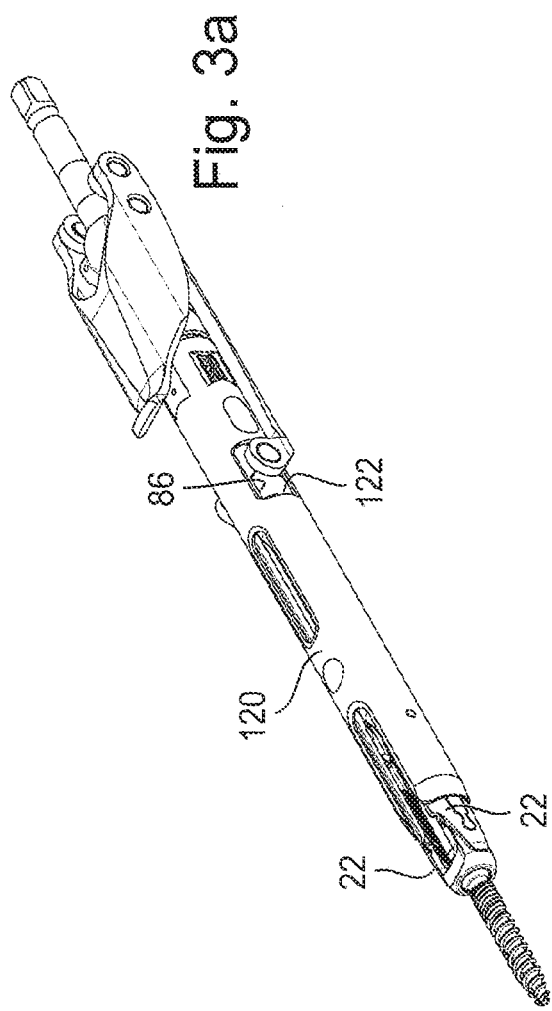
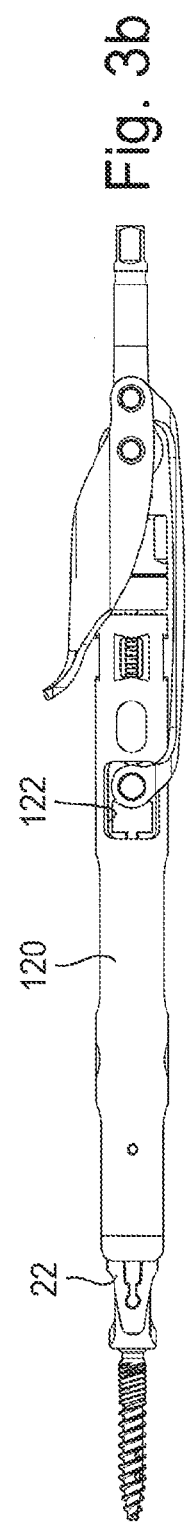
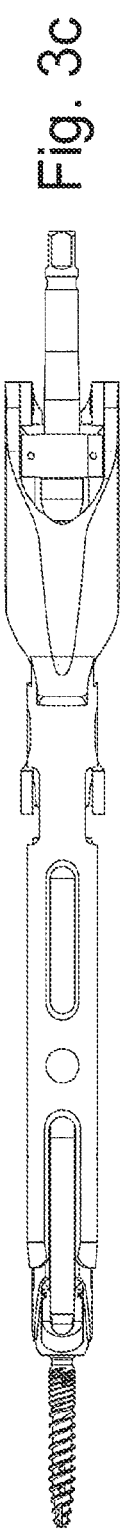

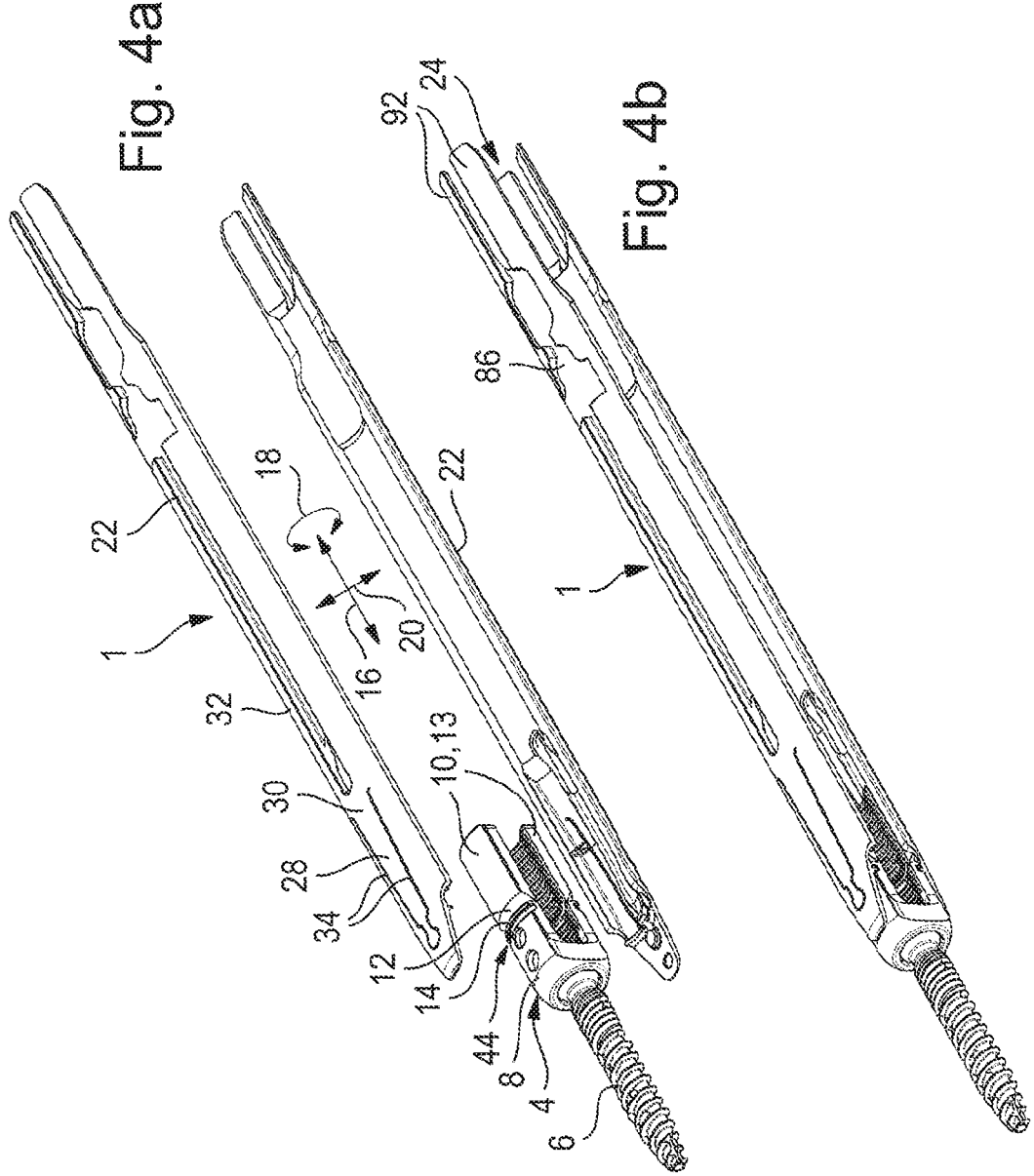

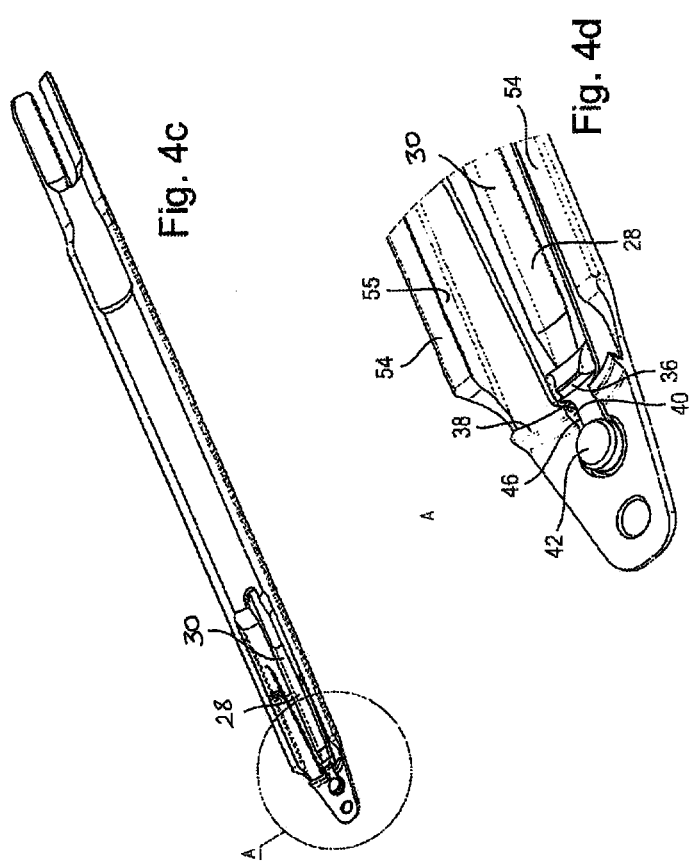

EXTENSION DEVICE FOR A BONE SCREW AND SCREWDRIVER INSTRUMENT

This application claims priority to German Patent Application No. 10 2017 120 619.1 filed on Sep. 7, 2017.

DESCRIPTION

The invention refers to an extension device for a bone screw, in particular for a pedicle screw, in particular in the minimally invasive spine surgery, and to a screwdriver instrument connectable with the extension device, with an axial longitudinal direction, a circumferential direction concentric thereto and a radial direction, wherein the extension device is extended in the axial longitudinal direction and forms an access channel to the bone screw and is removably connectable to the bone screw and wherein the screwdriver instrument has a shank, which may be positioned in the axial longitudinal direction within the access channel and which may be non-rotatably coupled to a tool application point of the bone screw.

The extension devices in question may comprise a sleeve-like housing part, for example, which may be removably connected to a head of the bone screw and which delimits a preferably tunnel-shaped access channel to the bone screw. The surgeon may access the bone screw through this access channel and in particular couple a screwdriver instrument to a tool application point of the bone screw. However, also extension devices may be conceived, which are formed by at least one shell part.

The object of the present invention is to provide a screwdriver instrument for a bone screw, or an assembly or a system comprising an extension device and a screwdriver instrument for a bone screw, wherein the screwdriver instrument may be connected to the extension device and a tool application point of the bone screw in an operatively secure way and may also be perceived as simple and advantageous to operate by a surgeon.

This object is achieved by an extension device and a screwdriver instrument of said type according to the invention in that the screwdriver instrument comprises a toggle lever mechanism having a first and second lever arm, which are pivotally connected to each other through a common articulation point, that the first lever arm may be removably applied, in the area of its free end, at a first pivot bearing point on the extension device and is pivotally mounted and axially supported in the applied state, and that the second lever arm is pivotally mounted and axially supported at a second pivot bearing point on the shank, that the first lever arm is elastically and longitudinally extendable, and that this longitudinal extensibility and a distance between the second pivot bearing point and the common articulation point of the lever arms are adapted to each other in such a way that when manually tilting the second lever arm in the direction of a parallel alignment with the axial longitudinal direction, a dead center is overcome, and the toggle lever mechanism reaches a tilt-stable position, in which the shank of the screwdriver instrument is forced in the axial direction against the tool application point of the bone screw.

Due to the inventive configuration of the extension device and of the screwdriver instrument with a toggle lever mechanism, the instrument may be brought, through a single manual adjusting movement in the form of a pivoting of the second lever arm, into a correct operating position on the bone screw and on the extension device, which is removably connected to the bone screw. Due to the axial adjusting force, which is applied by the toggle lever mechanism and through which the screwdriver instrument is forced in the axial direction against the tool application point of the bone screw, the instrument is held non-rotatably and, due to the biasing, in an operatively secure way, in its proper mounting and actuating position on the extension device. This allows the surgeon, by holding and actuating the screwdriver instrument, to simultaneously manipulate the extension device and the bone screw in a correct way.

According to a preferred embodiment of the invention, the toggle lever mechanism is configured in a way that the first lever arm has lateral bearing plates, which allow the arm to laterally enclose the extension device, and the first lever arm with said lateral bearing plates forms the first pivot bearing point to the extension device. Thereby the lever arm encloses the extension device with its lateral bearing plates, thus allowing the lever arm to be pivotally coupled to the extension device.

To this end it is advantageous if bearing pins are formed on the lateral bearing plates of the first lever arm, which pins protrude in the direction of the extension device. These bearing pins may be removably or fixedly connected to the bearing plates, or they may only rotatably pass through the bearing plates.

The longitudinal extensibility of the first lever arm may be obtained in different ways. For example, to this end, elastically extensible materials may be used, or the first lever arm may be configured with an elastically yielding region. According to a further preferred embodiment, the toggle lever mechanism is configured in such a way that the first lever arm is provided with an elastic longitudinal extensibility, in that it is provided with a longitudinal portion essentially extending in the axial longitudinal direction, and which is however also slightly arcuate, wherein the longitudinal extensibility is thereby achieved. This slightly arcuate profile of the longitudinal portion allows a simple longitudinal extensibility of the first lever arm, which also allows the toggle lever mechanism to reach a tilt-stable position beyond its dead center.

It may also be advantageous if the first lever arm is provided with a longitudinal portion, which is essentially extending in the axial longitudinal direction and, at one or both ends, with a portion, which extends transversely or obliquely with respect to the axial longitudinal direction. Also, in this way a kind of arcuate or trapezoidal shape may be provided, which may provide a longitudinal extensibility of the first lever arm. In particular, an additional longitudinal extensibility may be thus achieved, if a longitudinal extensibility is provided in some other way, i.e. in particular due to a slight arcuate shape of the longitudinal portion.

It may also be conceived that said portion of the first lever arm, which extends transversely or obliquely with respect to the axial longitudinal direction, forms a bearing plate for the lever arm.

It may also be convenient and advantageous if the second lever arm is provided with a bearing plate, in which the common articulation point is formed with the first lever arm and the second pivot bearing point is provided with the shank, wherein the common articulation point and the second pivot bearing point in the closed state of the toggle lever mechanism are approximately positioned on a line in the axial longitudinal direction.

In order to provide the second pivot bearing point, the second lever arm is coupled, in any desirable way, pivotally and either removably or fixedly, to the shank of the screwdriver instrument. To this end, bearing pins, posts or similar pivotable coupling elements may be used again between the components. It may also be advantageously conceived, that the second pivot bearing point comprises a component, which is in particular removable from the shank and is provided with a passage opening, which component may be inserted in the axial longitudinal direction on the shank and may be non-rotatably or rotatably fixed and axially supported on the shank in a predetermined or predeterminable position, and that the second lever arm is pivotally articulated to this component. In this way, said removable component may simplify the mounting of the components.

The lever arms may be configured as essentially flat material portions, optionally having bearing plates extending therefrom. It is also advantageous, if the first and/or second lever arm have a flat rounded form, in that they partially enclose both shell parts from radially outside. Thereby the haptic properties or ergonomics of the screwdriver instrument may be optimized. It is also advantageous if the second lever arm has a manually graspable region, which is formed, with respect to the second pivot bearing point, on the half of the second lever arm which is facing away from the common articulation point, and which is formed radially on the outer side. When fixing the instrument to the extension device, only a subsequent adjusting pressure provided by the closing hand has then to be applied on the instrument or on the second lever arm.

It is also advantageous if the second lever arm is provided, at its free end, with an end portion, which is oblique with respect to the axial longitudinal direction and protrudes radially outwards, and which may be grasped radially from the inside, in order to move the lever arm from its closed position parallel to the axial longitudinal direction to a release position, beyond the dead center of the toggle lever mechanism. It may be advantageous, if the extension device comprises a sleeve-shaped housing part, which delimits the access channel to the bone screw, and that the first pivot bearing point is formed on the sleeve-shaped housing part.

Alternatively, it may be advantageous, if the extension device comprises at least one shell part, which may be fixed, in a removable way, to the head of the bone anchor, however in a longitudinally rigid and also non-rotatable way, and that the first pivot bearing point is formed on the shell part.

In a further development of this concept, it may be advantageous, if the extension device comprises two preferably separate shell parts, which extend in the longitudinal direction and which in the removably fixed state, together delimit the access channel to the bone screw, and that the first pivot bearing point is formed on one of the shell parts or preferably in the circumferential direction between the shell parts, i.e. it is formed by both shell parts.

In this case it is advantageous if the first lever arm of the screwdriver instrument is thus supported on both shell parts, the first lever arm engaging with protruding bearing pins into a respective shell part or engaging a respective shell part and being rotatably supported there in the axial longitudinal direction.

In a further development of this concept it is advantageous if the first pivot bearing point is delimited by flanks of the respective shell part, which converge preferably in a rounded form in the proximal direction. In this way, the screwdriver instrument may be guided in its correct connection and supporting position on both shell parts. Thereby a certain self-centering is obtained while fixing the instrument to the shell parts.

Furthermore, it may be advantageous if the flanks of the respective shell part delimit an engaging opening in the shell part. This engaging opening is preferably also extending in the circumferential direction. It thus allows the first lever arm to move transversely with respect to the axial longitudinal direction into the respective engaging opening and then to move, in the proximal direction, into the pivot bearing point.

Further details, characteristics and advantages of the invention are provided by the attached claims and the graphic representation and following description of a preferred embodiment of the inventive extension device with a screwdriver instrument and a bone screw.

In the drawing, in particular:

FIGS. 1a-f show various views of an extension device, which is removably fixed to a bone screw and of a screwdriver instrument, which is removably fixed to the extension device;

FIGS. 2a-f show various views of the screwdriver instrument of FIGS. 1a-f;

FIGS. 3a-d show various views of an extension device, which is removably fixed to a bone screw and of a screwdriver instrument, which is removably fixed to the extension device, according to a further embodiment;

FIGS. 4a-d show various views of the bone screw and of the extension device.

FIGS. 1a-f show an inventive embodiment of an extension device 1 and of a screwdriver instrument 2. The extension device 1 is represented in a removable mounting connection on a bone anchor 4 illustratively formed by pedicle screw.

As shown in FIGS. 4a-d, the bone anchor 4 comprises a screw shank 6, which is positioned, in a polyaxially pivotable way with respect to a head 8 of the pedicle screw 4, which has a U-shape in the lateral view. The head 8 is for example a so called "long head", which is formed with longer branches 10, wherein nominal fracture point 12 is provided, in which the long head may be shortened when mounted, in that a head part 13 may be cut off. Regardless thereof, the head 8 of the bone anchor 4 comprises, as known per se, a region 14, which may be engaged from behind, which is formed by an undercut groove on the outer circumference of the head 8. The engageable region 14 of the head 8 may be provided, as described in the disclosure of the patent application DE 10 2014 225 327.6 of the applicant, the content of which is included in the disclosure of the present application.

The extension device 1 comprises an axial longitudinal direction 16, a circumferential direction 18, concentric thereto, and a radial direction 20, which all refer to the head 8 of the bone anchor 4. The extension device 1 comprises, in the exemplary embodiment, two mutually separate shell parts 22 extending in the longitudinal direction 16, which parts are illustratively and preferably corresponding to each other. The shell parts 22 are essentially rigid and torsion-stable, in that they are almost form-stable, although this does not rule out a slight irrelevant deformability, in particular due to the length. The shell parts 22 may also be removably fixed to the head 8 of the bone anchor 4, as will be described in the following, and then form an operating channel 24 delimited by the same, through which the surgeon may access the bone anchor 4 and the operational area by means of further instruments.

A respective shell part 22 is essentially dimensionally stable, wherein it however comprises, in the example shown, a first elastic element 28, which extends in the axial longitudinal direction 16 and may be deflected transversely thereto approximately in a radial outwards direction. The elastic element 28 in the embodiment shown is illustratively integrally formed with the shell part 22 and is integrally connected at its proximal end 30 to a wall 32 of the shell part 22. The elastic element 28 is delimited by a material-free slit 34 in the wall 32 of the shell part 22. The material-free slit 34 terminates at its proximal end in a curved way, thus causing a uniform transmission of tensions into the shell part 22. The elastic element 28 also has a support region 36, which protrudes radially and inwardly, through which the elastic element 28 and thus the shell part 22 may be supported in the axial and longitudinal direction 16 against the head 8 of the bone anchor 4. This support region 36 is positioned, in the axial and longitudinal direction 16 for example proximally to a radial protrusion 38 of the shell part 22. The radial protrusion 38 is formed as an inwardly protruding rib in the circumferential direction 18, which rib also has an extension in the proximal direction, in order to engage in the undercut region 14 on the head of the bone anchor. The extension of the radial protrusion 38 in the circumferential direction 18 is best shown in FIG. 4d. The radial protrusion 38 in the exemplary embodiment of FIGS. 4a-d has a central interruption 40, so that the elastic element 28 may extend in the axial and longitudinal direction 16 distally through the radial protrusion 38. It may also end before the radial protrusion 38. In the distal region with respect to the radial protrusion 38 in the example shown, the elastic element 28 comprises an engagement region 42 radially and inwardly protruding, which may engage in an engagement recess 44 on the head 8 of the bone anchor 4 and may provide an additional form-fitting connection between the shell part 22 and the bone anchor 4. The elastic element 28 is also formed in a way that in the region of the central interruption 40 of the radial protrusion 38 it is provided with a tapering or restriction 46, i.e. it is thinner in the circumferential direction in this position. As already described, the corresponding shell part 22 is removably but form-fittingly held on the head 8 of the bone anchor 4 with respect to all degrees of freedom in that, as best shown in FIGS. 4a-d, it hooks from behind the undercut region 14 of head 8 of bone anchor, with its radial protrusion 38, in the longitudinal direction 16 and in the radial direction 20 and abuts in the opposite direction with its supporting region 36 axially against head 8. In above said embodiment, the elastic element 28 also engages with its distal engagement region 42 in the engagement recess 44 on head 8. FIG. 3b shows that the respective shell part 22 has two inwardly recessed longitudinal edge regions 54, with which it abuts with lateral support surfaces 55 of opposite sides in the circumferential direction 18 against legs 10 of head 4 of bone anchor. The thin part 22 thus encloses the legs 10 essentially at least almost without play and is thus non-rotatably head in the circumferential direction 18 in addition to the action of the engaging elements.

Thus, an operative connection having a form-fit with respect to all degrees of freedom is achieved, which may be released in that the elastic element 28 of the respective shell part 22 is outwardly deviated in the radial direction 20. This may be achieved in that the elastic element 28 is accessed by means of a release instrument, not shown.

On the extension device 1 formed by the two shell parts 22 the screwdriver instrument 2 is removably disposed.

The screwdriver instrument 2 comprises an oblong shank 60 and a toggle lever mechanism 62, which is pivotally connected to the shank 60. The toggle lever mechanism 62 comprises a first lever arm 64 and a second lever arm 66, which are pivotally connected to each other by means of a common articulation point 68. The first lever arm 64 may be applied in a pivoting and removable way at a first pivot bearing point 72 on the extension device 1, and is supported in the axial and longitudinal direction 16. The second lever arm 66 is pivotally supported at a second pivot bearing point 74 on the shank 60 and is also axially supported. The first lever arm 64 is elastically and longitudinally extensible, wherein this longitudinal extensibility and a distance between the second pivot bearing point 74 and the common articulation point 68 of both lever arms 64, 66 are adapted to each other in a way that when manually rotating the second lever arm 66 in the direction of arrow 76 (see FIG. 1e) a dead center of the toggle lever mechanism 62 is overcome and the toggle lever mechanism reaches a tilt-stable position, in which the shank 60 of the screwdriver instrument 2 is forced in the axial direction 16 against the tool application point of the bone anchor 4.

FIGS. 2a to f show the components of the screwdriver instrument 2. In FIG. 2b, a distal end 78 of shank 60 is formed by a rotational coupling means 80. It may be used, complementarily, in the tool application point of bone anchor 4 for achieving a rotational coupling.

The first lever arm 64 comprises a longitudinal portion 81 and on its free ends 70 lateral bearing plates 82, with which it laterally covers both shell parts 22. Bearing pins 84 protruding in the direction of the extension device 1 are provided on these lateral bearing plates 82. The first lever arm 64 engages with these lateral bearing plates 82 and bearing pins 84 in a respective engagement opening 86 (see FIG. 1d). This engagement opening 86 is delimited by flanks 88, which converge, in a rounded way, in the proximal direction 90. Thus, the first pivot bearing point 72 is formed, in that the lateral bearing plates 82 are rotated with their bearing pins 84 transversely to the axial longitudinal direction (arrow 92) into the respective engagement opening 86 of the shell parts 22 and are then moved in the proximal direction 90 against the converging flanks 88 are finally axially abutting against the same. In order to form the common articulation point 88, the first lever arm 64 comprises at its further free end 94 also lateral bearing plates 96, wherein bearing pins 98 are also provided, which are rotatably coupled with lateral bearing plates 100 on the second lever arm 66.

The second pivot bearing point 74 between the second lever arm 66 and the shank 60 is formed, for example, in that a component 102, which may be removed from the shank 60, may be inserted with a passage opening 104 on the shank 60, and may be fixed on the shank 60 by means of bearing pins 108 which engage in a transverse opening 106 of the shank 60. In the example shown, these bearing pins 108 radially pass through the second lever arm 66 outwards into the region of its lateral bearing plates 100. The bearing plates 100 are formed here by a passage opening 110.

If, in this case, starting from the initial situation of FIG. 1e, a manual pressure is exerted on a manually graspable region 112, then the second lever arm 66 may be rotated in the direction of arrow 76, whereby the first lever arm 64 axially abuts against the first pivot bearing point 72 and is slightly expanded in the axial longitudinal direction 16, so that a dead center of the toggle lever mechanism 62 may be overcome. Thus, an axial adjustment pressure within the shank 60 is transmitted in the direction of the tool application point of the bone anchor 4. The components of the toggle lever mechanism are adapted to each other so that the toggle lever mechanism 62, after overcoming a dead center, is positioned in a tilt-stable position. In this position shown in FIG. 1f, the extension device 1 and the screwdriver instrument 2 form a unit, in which they are rigidly connected to each other and with the bone anchor 4.

In order to release the screwdriver instrument 2, the second lever arm 66 is provided, at its free end, with a portion 114, which protrudes obliquely with respect to the axial and longitudinal direction 16 in an outward direction, which portion may be grasped from the inside, in order to move the lever arm 66 again in a release position, i.e. against the arrow 76.

The screwdriver instrument 2 may be positioned on and removed from the extension device 1, which is already coupled with the bone anchor, in a particularly simple and stable manner. To this end, the shank 60 of the screwdriver instrument 2 is inserted into the access channel 24 until its rotational coupling means 80 engages in the tool application point of the bone anchor 4, and then the first lever arm 64 is rotated into the engagement opening 86, transversely to the longitudinal direction and then pulled by closing the second lever arm 66 in the direction of the arrow 76 against the first pivot bearing point 72.

FIGS. 3a to d show a further embodiment, which differs from the preceding in that the extension device 1 not only comprises the two shell parts 22 but an additional sleeve-shaped housing part 120, which may be inserted on both shell parts 22 in the axial and longitudinal direction 16. In the inserted state, the sleeve-shaped housing part 120 may be locked with one or both shell parts 22, so that it is securely but removably connected to the shell parts. As shown in FIGS. 3a to c, the sleeve-shaped housing part is formed with a cantilevered recess 122 in the region of the engagement opening 86 of the shell parts 22. Thus, the screwdriver instrument 2 may be positioned, as previously described, on the shell parts 22.

In an embodiment which is not shown, it may also be conceived that instead of the two shell parts 22, a single sleeve-shaped housing part, for example, is removably positioned on the head of the bone anchor 4, and the screwdriver instrument may then be positioned over a first pivot bearing point on this single sleeve-shaped housing part.

The invention claimed is:

1. An extension device (1) for a bone screw (4) and with a screwdriver instrument (2) connectable to the extension device (1), having an axial longitudinal direction (16), a circumferential direction (18), which is concentric thereto, and a radial direction (20), wherein the extension device (1) extends in the axial longitudinal direction (16) and forms an access channel (24) to the bone screw (4) and which is capable of being removably fixed to the bone screw (4), and wherein the screwdriver instrument (2) has a shank (60), which is capable of being positioned in the axial longitudinal direction (16) within the access channel (24) and which is capable of being non-rotatably coupled to a tool application point of the bone screw (4), and wherein the screwdriver instrument (2) comprises a toggle lever mechanism (62) having a first and a second lever arm (64, 66), which are pivotally connected to each other through a common articulation point (68), that the first lever arm (64) is capable of being removably applied, in the region of its free end (70), at a first pivot bearing point (72) on the extension device (1), and is pivotally mounted and axially supported in an applied state, and that the second lever arm (66) is pivotally mounted and axially supported at a second pivot bearing point (74) on the shank (60) such that the first lever arm (64) has an elastic longitudinal extensibility, and that this longitudinal extensibility and a distance between the second pivot bearing point (74) and the common articulation point (68) of the lever arms (64, 66) are adapted to each other such that when manually pivoting the second lever arm (66) in a direction of a parallel alignment with the axial longitudinal direction (16), a dead center is overcome, and the toggle lever mechanism (62) reaches a tilt-stable position, in which the shank (60) of the screwdriver instrument (2) is forced in the axial direction (16) against the tool application point of the bone screw (4), and wherein the second lever arm (66) has a bearing plate (100), in which the common articulation point (68) is formed with the first lever arm (64) and the second pivot bearing point (74) is formed with the shank (60), wherein the common articulation point (68) and the second pivot bearing point (74) are positioned on a line in the axial longitudinal direction (16), in a closed state of the toggle lever mechanism (62).

2. The extension device and screwdriver instrument of claim 1, wherein the first lever arm (64) has lateral bearing plates (82), by which it is capable of laterally enclosing the extension device (1), and that the first lever arm (64) forms, with said lateral bearing plates (82), the first pivot bearing point (72) to the extension device (1).

3. The extension device and screwdriver instrument of claim 2, wherein on the lateral bearing plates (82) of the first lever arm (64), bearing pins (84) are formed, which protrude in a direction of the extension device.

4. The extension device and screwdriver instrument of claim 3, wherein the first lever arm (64) engages, with the protruding bearing pins (84), into the extension device (1), or engages the extension device (1), and is rotatably supported there in the axial longitudinal direction (16).

5. The extension device and screwdriver instrument of claim 1, wherein the first lever arm (64) is provided with the elastic longitudinal extensibility, in that it is provided with a longitudinal portion (81), which extends in the axial longitudinal direction (16) and which also has an arcuate profile.

6. The extension device and screwdriver instrument of claim 1, wherein the first lever arm (64) has a longitudinal portion, (81) which extends in the axial longitudinal direction (16) and a portion at one or both ends (70, 94), which extends transversely or obliquely with respect to the axial longitudinal direction (16).

7. The extension device and screwdriver instrument of claim 6, wherein the portion of the first lever arm (64) extending transversely or obliquely with respect to the axial longitudinal direction forms a bearing plate (82).

8. The extension device and screwdriver instrument of claim 1, wherein the second pivot bearing point (74) comprises a component (102), with a passage opening (104), which is insertable on the shank (60) in the axial longitudinal direction (16) and which is capable of being non-rotatably or rotatably fixed and is axially supported on the shank (60) in a predetermined or predeterminable position and that the second lever arm (66) is pivotally articulated to this component (102).

9. The extension device and screwdriver instrument of claim 1, wherein the second lever arm (66) has a manually graspable region (112), which is formed, with respect to the second pivot bearing point (74), on a half of the second lever arm (66), which is facing away from the common articulation point (68) and radially on an outside.

10. The extension device and screwdriver instrument of claim 1, wherein the second lever arm (66) has, at its free end an end portion (114), which protrudes obliquely relative to the axial longitudinal direction and radially outwards, and which is capable of being grasped radially from an inside, in order to move the lever arm (66) from a closed position parallel to the axial longitudinal direction (16) into a release position.

11. The extension device and screwdriver instrument of claim 1, wherein the extension device (1) comprises a sleeve-shaped housing part (120), which delimits the access channel (24) to the bone screw (4) and that the first pivot bearing point (72) is formed on the sleeve-shaped housing part (120).

12. An extension device (1) for a bone screw (4) and with a screwdriver instrument (2) connectable to the extension device (1), having an axial longitudinal direction (16), a circumferential direction (18), which is concentric thereto, and a radial direction (20), wherein the extension device (1) extends in the axial longitudinal direction (16) and forms an access channel (24) to the bone screw (4) and which is capable of being removably fixed to the bone screw (4), and wherein the screwdriver instrument (2) has a shank (60), which is capable of being positioned in the axial longitudinal direction (16) within the access channel (24) and which is capable of being non-rotatably coupled to a tool application point of the bone screw (4), and wherein the screwdriver instrument (2) comprises a toggle lever mechanism (62) having a first and a second lever arm (64, 66), wherein the first and/or second lever arm (64, 66) are flatly rounded such that radially from an outside they partially enclose two mutually separate shell parts (22) of the extension device which extend in the longitudinal direction (16), and which form the access channel (24) delimited by the shell parts (22) and which first and/or second lever arm (64, 66) are pivotally connected to each other through a common articulation point (68), that the first lever arm (64) is capable of being removably applied, in the region of its free end (70), at a first pivot bearing point (72) on the extension device (1), and is pivotally mounted and axially supported in the applied state, and that the second lever arm (66) is pivotally mounted and axially supported at a second pivot bearing point (74) on the shank (60) such that the first lever arm (64) has an elastic longitudinal extensibility, and that this longitudinal extensibility and a distance between the second pivot bearing point (74) and the common articulation point (68) of the lever arms (64, 66) are adapted to each other such that when manually pivoting the second lever arm (66) in the direction of a parallel alignment with the axial longitudinal direction (16), a dead center is overcome, and the toggle lever mechanism (62) reaches a tilt-stable position, in which the shank (60) of the screwdriver instrument (2) is forced in the axial direction (16) against the tool application point of the bone screw (4).

13. An extension device (1) for a bone screw (4) and with a screwdriver instrument (2) connectable to the extension device (1), having an axial longitudinal direction (16), a circumferential direction (18), which is concentric thereto, and a radial direction (20), wherein the extension device (1) extends in the axial longitudinal direction (16) and forms an access channel (24) to the bone screw (4) and which is capable of being removably fixed to the bone screw (4), and wherein the screwdriver instrument (2) has a shank (60), which is capable of being positioned in the axial longitudinal direction (16) within the access channel (24) and which is capable of being non-rotatably coupled to a tool application point of the bone screw (4), and wherein the screwdriver instrument (2) comprises a toggle lever mechanism (62) having a first and a second lever arm (64, 66), which are pivotally connected to each other through a common articulation point (68), that the first lever arm (64) is capable of being removably applied, in the region of its free end (70), at a first pivot bearing point (72) on the extension device (1), and is pivotally mounted and axially supported in the applied state, and that the second lever arm (66) is pivotally mounted and axially supported at a second pivot bearing point (74) on the shank (60) such that the first lever arm (64) has an elastic longitudinal extensibility, and that this longitudinal extensibility and a distance between the second pivot bearing point (74) and the common articulation point (68) of the lever arms (64, 66) are adapted to each other such that when manually pivoting the second lever arm (66) in the direction of a parallel alignment with the axial longitudinal direction (16), a dead center is overcome, and the toggle lever mechanism (62) reaches a tilt-stable position, in which the shank (60) of the screwdriver instrument (2) is forced in the axial direction (16) against the tool application point of the bone screw (4), and wherein the extension device (1) comprises at least one shell part (22), which is fixable in a removable way, and rigidly and also non-rotatably in the longitudinal direction (16), to a head (8) of the bone screw (4), and that the first pivot bearing point (72) is formed on the shell part (22).

14. The extension device and screwdriver instrument of claim 13, wherein the extension device (2) comprises two shell parts (22) extending in the longitudinal direction (16), which, in a removably fixed state on the bone screw (4), together delimit the access channel (24) to the bone screw (4).

15. The extension device and screwdriver instrument of claim 13 wherein the first pivot bearing point (72) is delimited by flanks (88) of the respective shell part (22), which converge in a proximal direction.

16. The extension device and screwdriver instrument of claim 15 wherein the flanks (88) of the respective shell part delimit an engagement opening (86) in the shell part (22).

17. The extension device and screwdriver instrument of claim 13, wherein the shell part (22) engages, in a removably fixed state, in the longitudinal direction (16) and also in the radial direction (20), behind an engageable region (14) on the head (8) of the bone screw (4), by employing a radial protrusion (38).

* * * * *